United States Patent
Fleischer et al.

(10) Patent No.: US 9,170,248 B2
(45) Date of Patent: Oct. 27, 2015

(54) OPERATING METHOD FOR A GAS SENSOR AND GAS SENSOR

(75) Inventors: Maximilian Fleischer, Hoehenkirchen (DE); Karsten Hiltawsky, Schwerte (DE); Erhard Magori, Feldkirchen (DE); Roland Pohle, Herdweg (DE); Oliver von Sicard, Munich (DE)

(73) Assignee: Robert Bosch GmbH, Stuttgart (DE)

( * ) Notice: Subject to any disclaimer, the term of this patent is extended or adjusted under 35 U.S.C. 154(b) by 93 days.

(21) Appl. No.: 13/981,799

(22) PCT Filed: Jan. 10, 2012

(86) PCT No.: PCT/EP2012/050294
§ 371 (c)(1),
(2), (4) Date: Dec. 12, 2013

(87) PCT Pub. No.: WO2012/100979
PCT Pub. Date: Aug. 2, 2012

(65) Prior Publication Data
US 2014/0109648 A1   Apr. 24, 2014

(30) Foreign Application Priority Data
Jan. 28, 2011  (DE) .......................... 10 2011 003 291

(51) Int. Cl.
*G01N 7/00* (2006.01)
*G01N 33/00* (2006.01)
*G01N 27/414* (2006.01)

(52) U.S. Cl.
CPC ........ *G01N 33/0026* (2013.01); *G01N 27/4141* (2013.01); *G01N 33/0037* (2013.01)

(58) Field of Classification Search
CPC ................. A61M 2230/005; A61M 2230/201; A61M 2230/208; A61M 2230/43; F01N 11/00; G01N 33/0009; G01N 33/0004; G01N 33/0027; G01N 33/0016; G01N 33/0006
USPC ................................................ 73/23.2, 31.05
See application file for complete search history.

(56) References Cited

U.S. PATENT DOCUMENTS

2004/0133116 A1 *  7/2004  Abraham-Fuchs et al. .. 600/532
2010/0001211 A1 *  1/2010  Huang et al. ............... 250/492.1

FOREIGN PATENT DOCUMENTS

CN    1347498 A    5/2002
CN    2566267 Y    8/2003

(Continued)

OTHER PUBLICATIONS

Tim H. Richardsona et al, Taking advantage of optical and electrical properties of organic molecules for gas sensing applications, Aug. 1, 2001 Elsevier Science B.V. Thin Solid Films, vol. 393, No. 1-2, p. 259-266.*

(Continued)

*Primary Examiner* — Peter Macchiarolo
*Assistant Examiner* — Mohammed Keramet-Amircola
(74) *Attorney, Agent, or Firm* — Maginot, Moore & Beck LLP

(57) ABSTRACT

The disclosure relates to an operating method for a gas sensor, in particular a gas sensor for detecting asthma. According to said method, nitrogen monoxide or nitrogen dioxide is detected in a measuring phase and the gas sensor is heated by a heating device in a desorption phase in order to accelerate desorption. The heating process is continued until the temporal alteration of the measuring signal of the gas sensor falls below a threshold value.

9 Claims, 2 Drawing Sheets

(56) References Cited

FOREIGN PATENT DOCUMENTS

| CN | 101300481 A | 11/2008 |
|---|---|---|
| CN | 101556257 A | 10/2009 |
| CN | 101825595 A | 9/2010 |
| DE | 198 14 857 A1 | 10/1999 |
| DE | 199 56 744 A1 | 6/2001 |

OTHER PUBLICATIONS

Sun et al., A room temperature supramolecular-based quartz crystal microbalance (QCM) methane gas sensor, Sensors and Actuators B: Chemical, Aug. 18, 2009, pp. 104-108, vol. 141, Issue 1.

International Search Report corresponding to PCT Application No. PCT/EP2012/050294, mailed Mar. 8, 2012 (German and English language document) (7 pages).

Mattmann M et al., "Pulsed gate sweep strategies for hysteresis reduction in carbon nanotube transistors for low concentration NO2 gas detection", Nanotechnology, vol. 21, No. 18, Apr. 14, 2010, p. 185501, IOP Publishing, Bristol, GB, XP020174857.

Richardson, T. H. et al., "Taking advantage of optical and electrical properties of organic molecules for gas sensing applications", Thin Solid Films, vol. 393, No. 1-2, Aug. 1, 2001, pp. 259-266, Elsevier Science B.V., XP004296464.

* cited by examiner

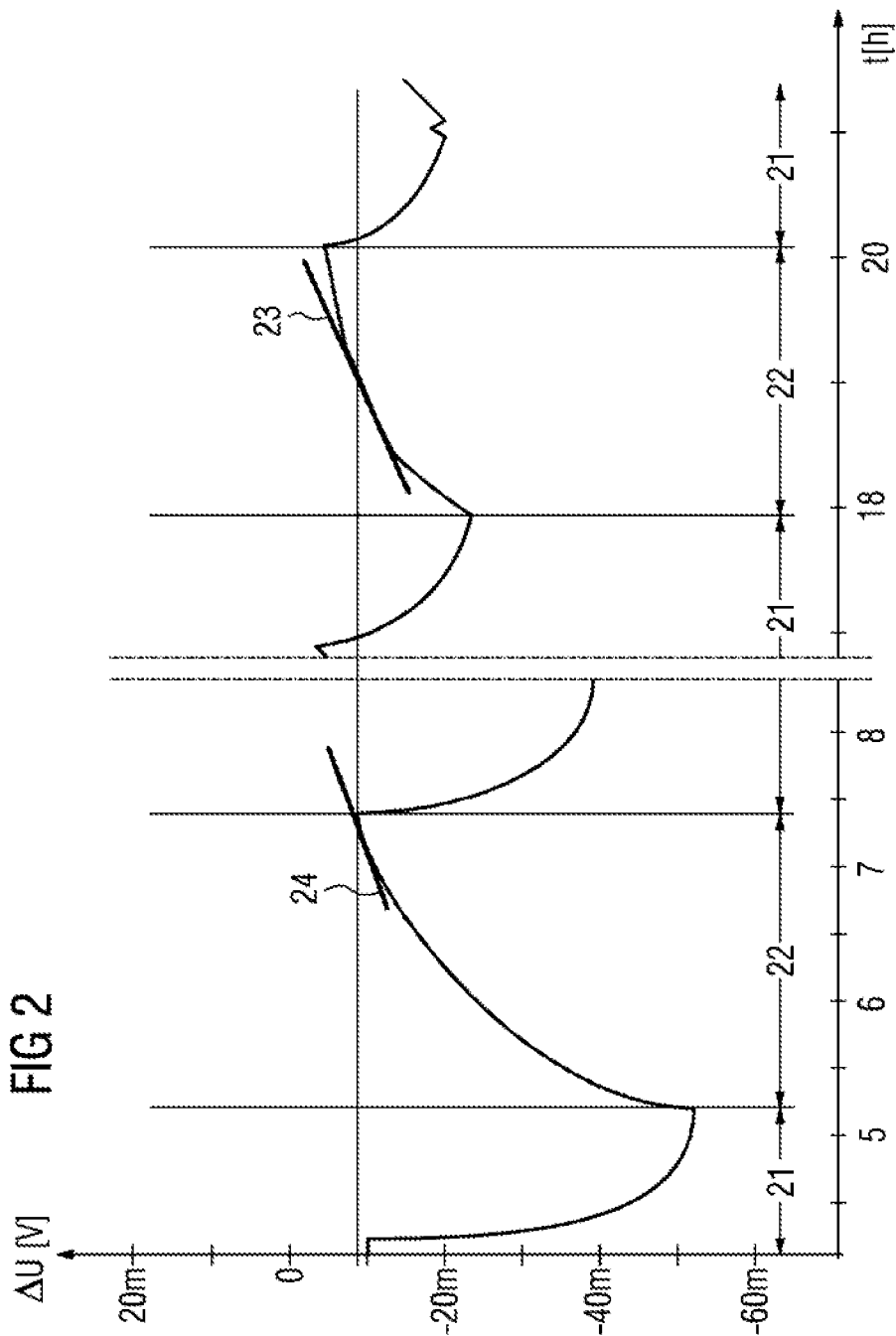

OPERATING METHOD FOR A GAS SENSOR AND GAS SENSOR

This application is a 35 U.S.C. §371 National Stage Application of PCT/EP2012/050294, filed on Jan. 10, 2012, which claims the benefit of priority to Serial No. DE 10 2011 003 291.6, filed on Jan. 28, 2011 in Germany, the disclosures of which are incorporated herein by reference in their entirety.

The disclosure relates to an operating method for a gas sensor, in particular for a gas sensor for detecting nitrogen monoxide or nitrogen dioxide, and to a gas sensor for carrying out the method, in particular for the determination of carbon monoxide or carbon dioxide.

BACKGROUND

Measuring the concentration of nitrogen monoxide (NO) in respired gas is an important means for optimizing the treatment of asthmatic conditions. One promising technology for the detection of nitrogen monoxide is an $NO_2$ sensor based on suspended gate FET technology. The structure of these sensors is known, for example, from the documents DE 19 814 857 or DE 19 956 744. Field effect transistor-based gas sensors have the advantage of simple production by using standard processes (CMOS) as well as a low energy demand in operation. Another advantage of these sensors is that they comprise a sensitive layer for the gas detection. The material of the sensitive layer may in this case be selected almost freely, and it is therefore possible to produce a range of different gas sensors on the same basis.

For the measurement of nitrogen dioxide, a layer of a porphyrin dye or phthalocyanine, in particular copper phthalocyanine, for example, has been found to be particularly promising. Nitrogen dioxide is adsorbed on this layer, and leads to a potential change and therefore to a measurable signal. If the nitrogen dioxide disappears from the ambient air, then the nitrogen dioxide bound on the surface of the copper phthalocyanine layer is desorbed and the signal falls off. One difficulty in this case is that the desorption of the nitrogen dioxide takes place very slowly. For instance, the t90 time at room temperature is more than 1 h.

SUMMARY

It is an object of the present disclosure to provide an operating method for a gas sensor, in particular for detecting nitrogen monoxide or nitrogen dioxide, which makes it possible to deal with the aforementioned problem in an improved way. It is another object of the disclosure to provide a corresponding gas sensor for detecting nitrogen monoxide or nitrogen dioxide.

In respect of the method, the object is achieved by a method having the features described herein. In respect of the gas sensor, the solution consists in a gas sensor having the features disclosed herein. Additional advantageous configurations are further described herein.

The operating method according to the disclosure for a gas sensor is expediently to be used with a gas sensor which alternates during its operating period between a measurement phase, in which it is exposed to the gas to be measured, and a regeneration phase in which the gas to be measured is desorbed. In other words, the measurement of the gas takes place discontinuously. This is achieved, for example, in the case of an asthma sensor in which the measurement takes place only during an expiration process. During the expiration phase, the gas sensor is exposed to nitrogen dioxide which is formed in the air from nitrogen monoxide, and during the regeneration phase the nitrogen dioxide is desorbed again.

According to the operating method disclosed herein, the gas sensor is to be operated during the measurement phase at room temperature or while being heated slightly, i.e. at temperatures of between 35° C. and 60° C. During the regeneration phase, on the other hand, the sensor is heated and brought to a temperature which is from 40° C. to 100° C. In a particular configuration, the sensor is even brought to a temperature of between 50° C. and 130° C. above the measurement temperature, in particular at least 100° C. above the measurement temperature.

Since the nitrogen oxide sensitivity of the sensitive material decreases with temperature, the effect thereby achieved is that a nitrogen oxide sensitivity which is as high as possible is advantageously obtained. Furthermore, the energy consumption of the sensor is relatively low as a result of this, since little electrical energy is required for heating during the measurement phase. On the other hand, the effect of the heating of the sensor carried out during the regeneration phase is that the desorption of the gas, for example nitrogen dioxide, takes place substantially more rapidly than would be the case at the temperature of the measurement phase. The sensor is therefore converted substantially more rapidly into a defined state in which a new measurement, which is independent or only slightly dependent on the history of the measurements, is possible. In other words, the sensor is heated out during the regeneration phase.

The proposed heating out is particularly advantageous in the case of a sensor such as the respired air sensor, since this entails not a continuous measurement but only an intermittent, discontinuous measurement. For sensors which carry out a continuous measurement, on the other hand, heating out is less advantageous. In a leak sensor, for example, the measurement values are considered continuously and heating out leads to a significant variation in the measurement value which, however, does not in fact correspond to any change in the quantity to be measured. In the case of continuously measuring sensors, this leads to difficulties in the signal evaluation.

It is particularly advantageous for the operating method to be used with a field effect transistor-based gas sensor (GasFET). This type of gas sensor allows problem-free measurement at room temperature together with problem-free electrical heating for the regeneration phase. At the same time, a GasFET allows very sensitive measurement and economical of nitrogen dioxide in its vicinity.

The gas sensor according to the disclosure is preferably a GasFET. It comprises a heater which allows heating of the sensor. The gas sensor according to the disclosure furthermore comprises a control device, which is configured in such a way that it carries out heating of the gas sensor in a regeneration phase.

In an alternative configuration, the gas sensor is configured in order to read out the electrical conductivity of a sensor layer as the measurement signal. In another alternative, the gas sensor is configured in order to read out changes in a mass or in a viscoelastic effect with a mass-sensitive transducer, for example QMB, SAW; CMUT, cantilever or FBAR, as the measurement signal.

In an advantageous configuration, the change in the measurement signal of the gas sensor as a function of time is determined in particular during the regeneration phase, i.e. during the heating out. This may, for example, be done in an analog-electronic or digital manner. In particular, the control device of the gas sensor is configured in order to calculate the change in the measurement signal as a function of time.

The change in the measurement signal as a function of time which is determined is used in an advantageous configuration by ending the heating out when the magnitude of the change in the measurement signal as a function of time falls below an establishable threshold value. In other words, when the establishable threshold value is fallen below, the heater is switched off and the gas sensor returns to room temperature or ambient temperature.

In this case, account is taken of the fact that initially rapid desorption of nitrogen dioxide from the sensitive layer of the gas sensor usually takes place after the end of a measurement. This desorption then slows down noticeably. The heating out accelerates the desorption considerably. When the magnitude of the change in the measurement signal as a function of time reaches the establishable threshold value, then a nitrogen dioxide surface condition of the sensitive layer of the gas sensor, established by the threshold value, has been reached.

Owing to the fact that the heating out is ended at this time, the temperature of the gas sensor decreases and the subsequent desorption of nitrogen dioxide slows down significantly. Therefore, an almost invariant starting point is defined for the subsequent measurement since the preloading with nitrogen dioxide is substantially established by the threshold value. In this way, the measurement accuracy for the subsequent measurements is improved significantly.

To this end, for example, the control device may be configured in order to monitor the change in the measurement values as a function of time and to switch off the heater when the threshold value is reached.

The change in the measurement value as a function of time which is established during the regeneration phase is used, according to another advantageous configuration, in order to increase the accuracy of the measurement value for the preceding measurement phase.

To this end, the value of the change as a function of time, in particular directly after the end of the measurement phase, is incorporated into the evaluation. Thus, besides the absolute value of the measurement signal at the end of the measurement phase, the change in the measurement value as a function of time after the end of the measurement phase is jointly taken into account.

BRIEF DESCRIPTION OF THE DRAWINGS

Preferred but in no way restrictive exemplary embodiments of the disclosure will now be explained in more detail with the aid of the figures of the drawing. The features are in this case represented in a schematized fashion.

FIG. 1 shows a measurement system and
FIG. 2 shows a measurement curve of a gas sensor.

DETAILED DESCRIPTION

Figure 1:
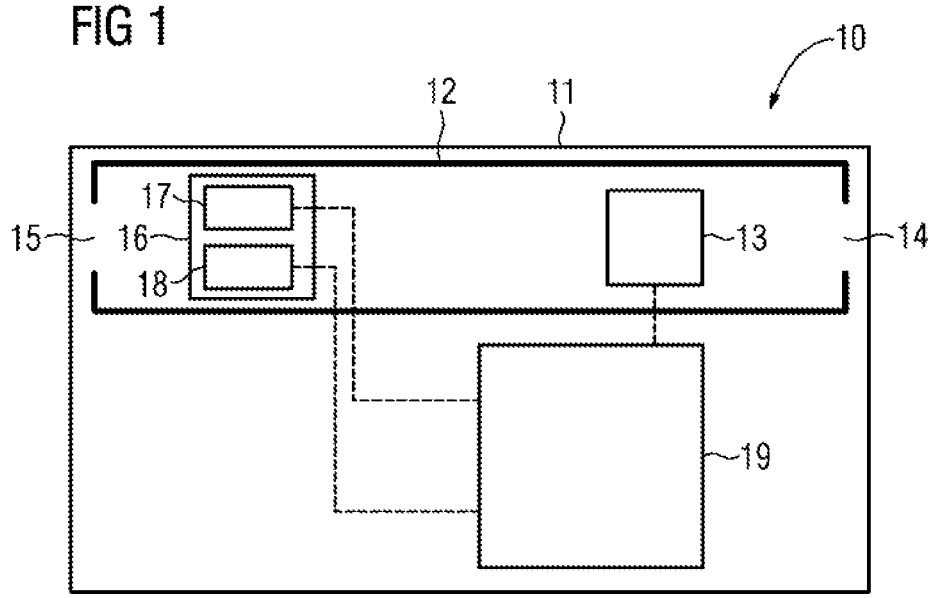

FIG. 1 shows a measurement system 10 for respired gas analysis. The measurement system 10 is contained in a housing, which is not shown in FIG. 1. The measurement system 10 comprises a main circuit board 11, on which the further elements are mounted. The further elements include a gas channel 12, which comprises an inlet opening 15 and an outlet opening 14. A pump unit 13 is accommodated in the gas channel 12. By means of the pump unit 13, air from outside the measurement system 10 can be drawn into the gas channel through the gas inlet 15. In this case, the air passes over a nitrogen dioxide sensor 16.

The nitrogen dioxide sensor 16 is a field effect transistor-based gas sensor. It comprises a sensitive layer 17 and a heater 18. Furthermore, the gas sensor 16 also comprises the typical electronic components for a field effect transistor.

The gas-sensitive layer 17 is in this case separated as a so-called suspended gate from the rest of the elements of the gas sensor 16 by a narrow air gap. In this exemplary embodiment, copper phthalocyanine is used as the material for the gas-sensitive layer 17.

The pump unit 13, the heater 18 and the electrical connections in the region of the sensitive layer 17 are connected to a control and evaluation device in the form of a microprocessor 19.

The microprocessor 19 controls the pump unit, so that a measurement can be carried out at a given time. Furthermore, the microprocessor 19 acquires measurement values from the gas-sensitive layer 17. Lastly, the microprocessor 19 controls the heater.

The microprocessor 19 is configured in order to carry out the following method during operation. When a measurement is imminent, the microprocessor 19 adjusts the heater 18 to an optimal value for a gas measurement. This optimal value may correspond to the ambient temperature, which means that the heater 18 is switched off. The optimal value for the temperature may also lie above the ambient temperature. In that case, the heater 18 is controlled accordingly in order to set this temperature in the gas sensor 16. The ambient temperature may be jointly measured in order to compensate for the effect of minor variations in the ambient temperature on the gas sensitivity, so as to increase the measurement accuracy.

The measurement values for the nitrogen dioxide measurement per se are then recorded and evaluated. Once the measurement phase is finished, the regeneration phase begins. In the regeneration phase, the nitrogen dioxide is desorbed from the surface of the sensitive layer 17. This causes reversal of the excursion of the measurement value of the sensitive layer 17 which occurred in the measurement phase. The measurement value in this case exhibits a change as a function of time, which is picked up and determined by the microprocessor 19.

During the regeneration phase, the microprocessor 19 regulates the heater 18 to an optimal temperature for heating out the gas-sensitive layer 17. The temperature used for this may, for example, be 100° C. or 150° C. or even more.

Subsequently, during the desorption step, the microprocessor 19 compares the change in the measurement signal as a function of time with an established threshold value. When the change in the measurement signal as a function of time falls below this threshold value, the desorption has taken place to a sufficient extent and the heating-out phase is ended in response to this, i.e. the microprocessor 19 turns the heater 18 off. The sensor 16, or the gas-sensitive layer 17, is now in a defined state. In order to minimize further changes of this state before the next measurement phase begins, the heater 18 may now be switched off.

The heating out up to a predeterminable threshold value of the change in the measurement signal as a function of time is illustrated in FIG. 2. FIG. 2 shows the profile of a measurement signal of a gas sensor 16 over a measurement period of a few hours. In this case, nitrogen dioxide and air without nitrogen dioxide are alternately brought into the vicinity of the sensor. The sensor signal of the gas-sensitive layer 17 exhibits corresponding excursions. An end of a respective heating-out phase is in this case always reached when the change in the measurement signal as a function of time, symbolized in FIG. 2 by the tangents 23, 24, reaches the threshold value.

The effect advantageously achieved by this is that the desorption of the nitrogen dioxide is accelerated by the heating-out step, without thereby incurring the disadvantage of a reduced sensitivity at high sensor temperatures during the measurement phase. The measurement per se during the measurement phase can be carried out at the optimal temperature in relation to the desired properties of sensitivity and response time as well as other criteria. Independently of the optimal measurement temperature, the desorption takes place at the optimal temperature for the desorption.

The change in the measurement signal as a function of time during the desorption of the nitrogen dioxide is dependent on the desorption rate of the nitrogen dioxide. This is determined by the heating-out temperature and the amount of nitrogen dioxide remaining on the surface of the sensitive layer 17. The higher the temperature and the higher the residual amount of nitrogen dioxide, the greater is the desorption rate and therefore the change in the measurement signal as a function of time. From this change as a function of time, it is therefore possible to deduce the residual amount of nitrogen dioxide on the sensor surface. This is taken into account by the microprocessor 19 when calculating the nitrogen dioxide concentration in a preceding measurement.

The invention claimed is:

1. An operating method for a gas sensor for the determination of nitrogen monoxide or nitrogen dioxide concentration, comprising:
    operating the gas sensor in a measurement phase during which a first gas having a first concentration of nitrogen monoxide or nitrogen dioxide to be analyzed is delivered to the gas sensor;
    operating the gas sensor in a regeneration phase during which a second gas with a second concentration of nitrogen monoxide or nitrogen dioxide that is lower than the first concentration is delivered to the gas sensor and the gas sensor is heated to a regeneration temperature which is greater than a measurement temperature by a heater;
    alternating operation of the gas sensor between the measurement phase and the regeneration phase;
    determining a change in the measurement signal of the gas sensor as a function of time; and
    operating the gas sensor unheated as soon as the change in the measurement signal as a function of time falls below a predetermined threshold value.

2. The method as claimed in claim 1, wherein the regeneration temperature is at least 100° C.

3. The method as claimed in claim 1, wherein the regeneration temperature is greater than the measurement temperature by between 50° C. and 130° C.

4. The method as claimed in claim 1, further comprising:
    determining a concentration value for nitrogen monoxide or nitrogen dioxide with reference to the change in the measurement signal as a function of time.

5. The method as claimed in claim 1, wherein the step of determining a change in the measurement signal of the gas sensor as a function of time occurs directly after the step of operating the gas sensor in the measurement phase.

6. A gas sensor for determining a concentration of nitrogen monoxide or nitrogen dioxide, comprising:
    a heater;
    a sensing element; and
    a control device configured to alternate operation of the gas sensor between a measurement phase and a regeneration phase,
    wherein in the measurement phase, a first gas to be analyzed is delivered to the gas sensor;
    wherein in the regeneration phase, a second gas with a lower concentration of nitrogen monoxide or nitrogen dioxide is delivered to the gas sensor;
    wherein the sensing element is configured to generate a measurement signal during both the measurement phase and the regeneration phase; and
    wherein the control device is further configured: (i) to determine a change in the measurement signal of the sensing element as a function of time; (ii) to control the heater to heat the gas sensor to a regeneration temperature which is greater than a measurement temperature during the regeneration phase; and (iii) to control the heater to operate the sensing element unheated as soon as the change in the measurement signal of the sensing element as a function of time falls below a predetermined threshold value.

7. The gas sensor as claimed in claim 6, wherein the the sensing element is configured as a field effect transistor-based gas sensor.

8. The gas sensor as claimed in claim 6, wherein:
    the sensor element includes a sensor layer; and
    the control device is configured to read an electrical conductivity of the sensor layer as the measurement signal.

9. The gas sensor as claimed in claim 6, wherein the sensing element is configured as a mass-sensitive transducer configured to sense a change in a mass or in a viscoelastic effect as the measurement signal.

* * * * *